United States Patent [19]

Iwata et al.

[11] 4,008,070
[45] Feb. 15, 1977

[54] METHOD FOR THINNING YOUNG FRUITS AND BLOSSOMS AND AGENT THEREFOR

[75] Inventors: Takashi Iwata, Kyoto; Kazuo Nakanishi, Osaka; Minoru Nagao, Kyoto; Seiichi Ishida; Yasuo Kamuro, both of Shiraoka, all of Japan

[73] Assignees: Nissan Chemical Industries Co., Ltd., Tokyo; Fujisawa Pharmaceutical Co., Ltd., Osaka, both of Japan

[22] Filed: Apr. 29, 1975

[21] Appl. No.: 572,706

Related U.S. Application Data

[63] Continuation-in-part of Ser. No. 404,758, Oct. 9, 1973, abandoned, which is a continuation of Ser. No. 179,589, Sept. 10, 1971, abandoned, which is a continuation-in-part of Ser. No. 749,599, Aug. 2, 1968, abandoned.

[30] Foreign Application Priority Data

Aug. 5, 1967   Japan .............................. 42-50122

[52] U.S. Cl. ........................................ 71/92; 71/96; 71/114; 260/310 C
[51] Int. Cl.² ........................................... A01N 9/22
[58] Field of Search .............. 260/310 C; 71/96, 92

[56] References Cited

UNITED STATES PATENTS 2,314,091   3/1943   Jones ................................. 71/114
2,701,251   2/1955   Fox et al. ............................. 71/96

OTHER PUBLICATIONS

Batjer, "Fruit Thinning with Chem. Sprays," (1951) CA45, pp. 7287–7288 (1951).
Hellman et al., "3-Indazoleacetic Acid, etc.," (1961), Phyton 17, pp. 11–13 (1961).

*Primary Examiner*—Glennon H. Hollrah
*Attorney, Agent, or Firm*—Wenderoth, Lind & Ponack

[57] ABSTRACT

Method for thinning young fruits and blossoms by applying to fruit trees, particularly citrus fruit trees an indazole compound of the formula:

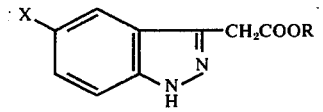

wherein R is hydrogen or a lower alkyl having 1 to 4 carbon atoms, and X is a halogen, or the salt thereof, and a thinning agent containing as the active ingredient the indazole compound as mentioned above.

10 Claims, No Drawings

METHOD FOR THINNING YOUNG FRUITS AND BLOSSOMS AND AGENT THEREFOR

This is a continuation-in-part application of the application Ser. No. 404,758, filed on Oct. 9, 1973, which is, in turn, a continuation application of the application Ser. No. 179,589, filed on Sept. 10, 1971, which is, in turn, a continuation-in-part application of the application Ser. No. 749,599, filed on Aug. 2, 1968, all now abandoned.

The present invention relates to a method for thinning young fruits and blossoms, and a thinning agent.

Hitherto, it has been known that naphthalene-$\alpha$-acetic acid (hereinafter, referred to as NAA) is effective for thinning young fruits and blossoms in citrus fruit trees. However, when NAA is used for the purpose, the harvested fruits show sometimes so-called "rind puffing", i.e. the rind of the fruits becomes larger than the contents of the fruits and a space occurs between the contents and the rind. Moreover, the NAA must be applied to the fruit trees within a very short period after the full blooming, for instance, before the physiological fruit drop.

Under the circumstances, the present inventors have extensively studied to find a chemical compound useful for thinning young fruits and blossoms having no such defects as in NAA, and have unexpectedly found that some specific indazole compounds are highly effective for such a purpose.

An object of the present invention is to provide a method for thinning fruits and blossoms.

Another object of the invention is to provide a method for applying an indazole compound (I) to fruit trees for the purpose of thinning fruits and blossoms.

A further object of the invention is to provide a thinning agent containing as the active ingredient an indazole compound (I).

These and other objects of the invention will be apparent from the description hereinafter.

The chemical compounds used in the present invention are 5-halo-1H-indazole-3-acetic acids and the lower alkyl esters thereof of the formula:

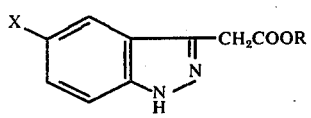  (I)

wherein R is hydrogen or a lower alkyl having 1 to 4 carbon atoms (e.g. methyl, ethyl, propyl, isopropyl, butyl or tert.butyl), and X is a halogen (e.g. chlorine or bromine).

When the indazole compounds of the formula (I) are free acids (I: R being hydrogen), those may be used in the form of salts. Examples of the salts are alkali metal salts (e.g. sodium or potassium salt), amine salts (e.g. dimethylamine or triethanolamine salt), ammonium salts, etc.

According to the present inventors' new findings, the indazole compounds of the formula (I) show an excellent effect on the thinning of young fruits and blossoms in various fruit trees, such as oranges, lemons, grapefruits, tangerines, apples, pears, plums, peaches, persimmon, etc., particularly in citrus fruit trees (e.g. oranges, lemons, limes, citrons, grapefruits, tangerines and pummelos), and can be applied to the trees within a long period after the full blooming, for instance, even after the physiological fruit drop. Moreover, the present indazole compounds can give good fruits having a comparatively uniform and moderate size without a rind puffing as observed in NAA.

Some of the test results from which the above findings have been conducted are shown below.

Test 1

Thinning of mandarin orange fruits:

Ethyl 5-chloro-1H-indazole-3-acetate and NAA were subjected to test. A designed concentration of an emulsion of the test compound prepared as in Example II was applied to three branches of mandarin orange trees elapsed 30 days after full blooming and having 60 to 100 fruits in such an amount as to wet the branches sufficiently. The numbers of the fruits on each branch before the application and one month after the application and the remaining percent of fruits calculated thereon are shown in Table 1.

Table 1

| Active ingredient | Concentration (ppm) | Before application | One month after application | Remaining percent (%) |
|---|---|---|---|---|
| Ethyl 5-chloro-1H-indazole-3-acetate | 200 | 100 | 9 | 9.0 |
|  | 400 | 70 | 6 | 8.6 |
|  | 800 | 106 | 5 | 4.7 |
| NAA | 300 | 100 | 10 | 10.0 |
| Untreated | — | 70 | 12 | 17.1 |

Test 2

Thinning of mandarin orange fruits:

Ethyl 5-chloro-1H-indazole-3-acetate was subjected to test. A 200 ppm concentration of the test compound was applied to mandarin orange trees on the 20th day after full blooming. The number of the fruits on each plot before the application and 40 days after the application and the remaining percent of fruits calculated thereon are shown in Table 2.

Table 2

| | Applied 20 days after full blooming | | | Untreated | | |
|---|---|---|---|---|---|---|
| Plot | Before application | 40 days after application | Remaining percent (%) | Before application | 40 days after application | Remaining percent (%) |
| 1 | 142 | 13 | 9 | 208 | 79 | 38 |
| 2 | 253 | 26 | 10 | 224 | 98 | 44 |

Test 3

5-Chloro-1H-indazole-3-acetic acid was subjected to test. A 800 ppm concentration of the test compound was applied to mandarin orange trees on the 30th day after full blooming. The numbers of the fruits on each plot before the application and 46 days after the application and the remaining percent of the fruits calculated thereon are shown in Table 3.

Table 3

| | Applied 30 days after full blooming | | | Untreated | | |
|---|---|---|---|---|---|---|
| Plot | Before application | 40 days after application | Remaining percent (%) | Before application | 40 days after application | Remaining percent (%) |
| 1 | 62 | 16 | | 61 | 16 | |

Table 3-continued

| | Applied 30 days after full blooming | | | Untreated | | |
|---|---|---|---|---|---|---|
| Plot | Before application | 40 days after application | Remaining percent (%) | Before application | 40 days after application | Remaining percent (%) |
| 2 | 88 | 5 | | 63 | 16 | |
| 3 | 60 | 10 | | 40 | 21 | |
| Total | 210 | 31 | 15 | 164 | 53 | 32 |

Test 4

Ethyl 5-chloro-1H-indazole-3-acetate was subjected to test. A designed concentration of the test compound was applied to mandarin orange trees on the 40th, 50th and 60th days after full blooming. The numbers of the fruits on each plot before the application and 15–38 days after the application were counted and the remaining percent of the fruits was calculated thereon. The results are shown in Table 4.

Table 4

| Concentration (ppm) of the test compound | Application date after the full blooming | | | Average |
|---|---|---|---|---|
| | 40th | 50th | 60th | |
| 100 | 34.1 | 18.6 | 37.7 | 30.1 |
| 200 | 32.2 | 15.7 | 34.6 | 27.5 |
| 300 | 30.8 | 15.5 | 28.5 | 24.9 |
| Untreated | — | | | 38.7 |

Test 5

Generation of ethylene in mandarin orange trees:

As the thinning effect of the present indazole compounds (I) is considered to be due to the ethylene produced thereby in leaves and in the absciss layer of fruits and blossoms and to be promoted proportionally with the amount of the produced ethylene, the amount of the ethylene was quantitatively determined.

Ethyl 5-chloro-1H-indazole-3-acetate, sodium 1H-indazole-3-acetate and NAA were subjected to the test. A 500 ppm concentration of the test compound was applied to mandarin orange trees aged 3 years, and the amount of ethylene generated from 24 to 48 hours after the application was quantitatively determined. In case of ethyl 5-chloro-1H-indazole-3-acetate, the amount of the produced ethylene was 13.5 mcg/g. In case of sodium 1H-indazole-3-acetate and NAA, it was 4.5 mcg/g and 8.5 mcg/g, respectively.

As understood from the above test results, the indazole compounds of the invention are effective in thinning young fruits and blossoms of fruits trees, particularly citrus fruits trees.

In the present invention, there is used as the active ingredient at least one of the indazole compounds of the formula (I). Specific examples of the indazole compounds are 5-chloro-1H-indazole-3-acetic acid, methyl 5-chloro-1H-indazole-3-acetate, ethyl 5-chloro-1H-indazole-3-acetate, 5-bromo-1H-indazole-3-acetic acid, ethyl 5-bromo-1H-indazole-3-acetate, etc. Preferred compounds are the one of the formula (I) wherein R is hydrogen or ethyl, and X is chlorine or bromine. The most preferred compounds are 5-chloro-1H-indazole-3-acetic acid and ethyl 5-chloro-1H-indazole-3-acetate.

The indazole compounds (I) of the present invention may be produced by a variety of methods. One of the typical procedures may consist of diazotating 2-amino-5-halo-cinnamic acid [Chem. Abst., 26, 1592], reducing the resulting diazonium salt and heating the resultant so as to accomplish ring closure, if necessary, followed by esterification.

Alternatively, the indazole compounds (I) may be prepared by halogenating 3-hydroxymethyl-1H-indazole [J. Am. Chem. Soc., 79, 5254 (1957)] with sulfuryl halide and thionyl halide, reacting the resulting 3-halomethyl-5-halo-1H-indazole with a cyanide, and subjecting the resulting 3-cyanomethyl-5-halo-1H-indazole to hydrolysis and/or esterformation.

The preparations of the present indazole compounds are illustrated by the following Examples.

EXAMPLE 1

Preparation of 5-chloro-1H-indazole-3-acetic acid:

To a suspension of 2-amino-5-chlorocinnamic acid (3.0 g) in water (35 ml), there is added conc. hydrochloric acid (11 ml). To the resulting solution cooled with ice, a solution of sodium nitrite (1.0 g) in water (2 ml) is dropwise added while stirring, and stirring is continued for 30 minutes. Anhydrous sodium sulfite (5.0 g) is portionwise added thereto. After stirring at room temperature for 1 hour, the resulting mixture is admixed with water (100 ml) and heated on an oil bath for 0.5 to 1 hour while refluxing. The reaction mixture is filtered. The collected material is washed with hot water. The washing water is combined with the filtrate and concentrated. The residue is crystallized from hot water to give 5-chloro-1H-indazole-3-acetic acid (0.7 g) as white needles melting at 205° C (decomp.)

In the same manner as described above, 5-bromo-1H-indazole-3-acetic acid is prepared, m.p. 192.5° – 193.5° C (decomp.)

EXAMPLE 2

Preparation of ethyl 5-chloro-1H-indazole-3-acetate:

3-Hydroxymethyl-1H-indazole (6.3 g) is added to a mixture of 2.5% of sulfuryl chloride and 97.5% of thionyl chloride (80 ml), and the resulting mixture is heated at 50° C for 6 hours. After allowing to stand overnight, the reaction mixture is concentrated under reduced pressure, admixed with methanol and again concentrated. The residue is washed out with benzene and filtered to collect 3-chloromethyl-5-chloro-1H-indazole (4.5 g) as white crystals melting at 150° to 155° C (decomp.).

A solution of 3-chloromethyl-5-chloro-1H-indazole (4.5 g) in ethanol (50 ml) is dropwise added to a solution of potassium cyanide (17 g) in water (10 ml) while stirring at 5° C, and the resulting mixture is stirred at room temperature for 2 hours and at 50° C for 2 hours. The reaction mixture is cooled and the precipitated potassium chloride is removed by filtration. The filtrate is concentrated under reduced pressure, admixed with water and extracted with ether. The ether layer is washed with water, dried over anhydrous magnesium sulfate and concentrated to give 3-cyanomethyl-5-chloro-1H-indazole (3.0 g) as resinous material.

A solution of 3-cyanomethyl-5-chloro-1H-indazole (3.0 g) in anhydrous ethanol (30 ml) is saturated with hydrogen chloride while stirring under cooling with ice. The resulting mixture is allowed to stand at room temperature overnight and refluxed for 3 hours. After removal of the solvent, the residue is admixed with water and extracted with ether. The ether extract is washed with water, dried over anhydrous magnesium sulfate and concentrated to give ethyl 5-chloro-1H-indazole- 3-acetate (2.3 g) as resinous material. When crystallized from a mixture of benzene and hexane, there are obtained colorless crystals melting at 75° to 76° C.

The indazole compounds (I) of the present invention can be applied to various fruit trees for thinning excessive fruits and blossoms so as to promote the growth of the remaining fruits. The active indazole compound is practically applied in any extended form having a concentration of 50 to 1,000 ppm, favorably of 100 to 800 ppm more favorably of 100 to 200 ppm, within a period of about three months from full blooming, usually of two weeks to 60 days after full blooming. Thus, the present indazole compound can be applied to even after the physiological fruit drop.

The active indazole compounds of the present invention may be used alone but usually extended with solid, liquid or gaseous carriers to formulate duct, wettable powder, solution, emulsion, aerosol or any other conventional preparations. Examples of the carriers are talc, clay, kaolin, kieselguhr, calcium carbonate, potassium chlorate, nitrate of sode, water, alcohol, benzene, acetone, etc. If necessary, there may be used any auxiliary agent such as spreader, emulsifier, surface active agent and the like. There may be also incorporated fungicide, insecticide, nematocide or the like.

Practical and preferred embodiments of the compositions are illustrated by the following Examples wherein parts are by weight.

EXAMPLE I

Solution:

5-Chloro-1H-indazole-3-acetic acid (1 part) is dissolved in ethanol (50 parts), and water (49 parts) is added thereto to prepare a solution. The solution is employed after diluting with water in 10 to 200 folds and admixing with a spreader (Nitten, made by Nissan Chemical Industries, Ltd.) in 0.03 to 0.05% concentration.

EXAMPLE II

Emulsion:

Ethyl 5-chloro-1H-indazole-3-acetate (10 parts), xylene (70 parts) and an emulsifier (Toximal 500, made by Sanyo Chemical Industries, Ltd.; 20 parts) are mixed uniformly to prepare an emulsion. The emulsion is employed after diluting with water in 100 to 2,000 folds.

What is claimed is:

1. A method for thinning young fruits and blossoms, which comprises applying to fruit trees an effective amount for thinning the fruits and blossoms of an indazole compound of the formula:

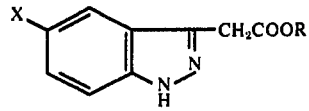

wherein R is a lower alkyl having 1 to 4 carbon atoms and X is chlorine or bromine within a period of 60 days after full blooming.

2. The method according to claim 1, wherein the indazole compound is applied in the form of solution or emulsion.
3. The method according to claim 1, wherein the indazole compound is applied within a period of two weeks to 60 days after full blooming.
4. The method according to claim 1, wherein the indazole compound is ethyl 5-chloro-1H-indazole-3-acetate.
5. The method according to claim 2, wherein the indazole compound is applied in a concentration of 100 to 800 ppm.
6. The method according to claim 2, wherein the indazole compound is applied in a concentration of 100 to 200 ppm.
7. A thinning agent for young fruits and blossoms containing as the active ingredient an indazole compound of the formula:

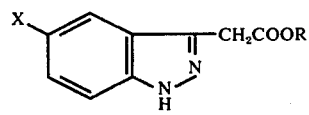

wherein R is a lower alkyl having 1 to 4 carbon atoms and X is chlorine or bromine and an inert carrier, said active ingredient being present in a concentration of 100 to 800 ppm.

8. The thinning agent according to claim 7, wherein the indazole compound is ethyl 5-chloro-1H-indazole-3-acetate.
9. The thinning agent according to claim 7, wherein the active ingredient is present in a concentration of 100 to 200 ppm.
10. Ethyl 5-chloro-1H-indazole-3-acetate.

* * * * *